US008987329B2

(12) United States Patent
Casey et al.

(10) Patent No.: US 8,987,329 B2
(45) Date of Patent: Mar. 24, 2015

(54) ORAL COMPOSITION COMPRISING A POLYUNSATURATED FATTY ACID AND SALICYLIC ACID FOR OBTAINING AN ANTIINFLAMMATORY EFFECT IN SKIN

(75) Inventors: John Casey, Sharnbrook (GB); Alexander Gordon James, Sharnbrook (GB); Gail Jenkins, Sharnbrook (GB); Linda Jane Wainwright, Sharnbrook (GB)

(73) Assignee: Conopco, Inc., Englewood Cliffs, NJ (US)

( * ) Notice: Subject to any disclaimer, the term of this patent is extended or adjusted under 35 U.S.C. 154(b) by 744 days.

(21) Appl. No.: 12/226,164

(22) PCT Filed: Apr. 5, 2007

(86) PCT No.: PCT/EP2007/053410
§ 371 (c)(1),
(2), (4) Date: Oct. 9, 2008

(87) PCT Pub. No.: WO2007/116027
PCT Pub. Date: Oct. 18, 2007

(65) Prior Publication Data
US 2009/0192126 A1 Jul. 30, 2009

(30) Foreign Application Priority Data

Apr. 12, 2006 (EP) .................................... 06252027
Feb. 12, 2007 (EP) .................................... 07102129

(51) Int. Cl.
| A01N 37/00 | (2006.01) |
| A61K 31/19 | (2006.01) |
| A01N 37/06 | (2006.01) |
| A61K 31/22 | (2006.01) |
| A61K 31/20 | (2006.01) |
| A61K 31/192 | (2006.01) |
| A61K 31/202 | (2006.01) |
| A61K 31/616 | (2006.01) |

(52) U.S. Cl.
CPC ............. *A61K 31/192* (2013.01); *A61K 31/202* (2013.01); *A61K 31/616* (2013.01)
USPC ............................ 514/557; 514/549; 514/560

(58) Field of Classification Search
USPC ................................................ 514/557, 549
See application file for complete search history.

(56) References Cited

U.S. PATENT DOCUMENTS

| 4,843,095 A | 6/1989 | Rubin |
| 5,130,061 A | 7/1992 | Cornieri et al. |
| 5,562,913 A | 10/1996 | Horrobin |
| 5,567,424 A | 10/1996 | Hastings |
| 5,698,595 A | 12/1997 | Boelle et al. |
| 5,876,737 A | 3/1999 | Schonrock |
| 5,976,606 A | 11/1999 | Koga et al. .................... 426/634 |
| 6,149,939 A * | 11/2000 | Strumor et al. ............... 424/464 |
| 6,335,038 B1 | 1/2002 | Cavazza ......................... 424/757 |
| 6,589,535 B2 | 7/2003 | Castelli et al. ............. 424/283.1 |
| 6,605,296 B1 | 8/2003 | Stuckler |
| 6,750,332 B1 | 6/2004 | Otto |
| 2002/0048798 A1* | 4/2002 | Avery et al. .................... 435/183 |
| 2002/0054918 A1 | 5/2002 | Murad ........................... 424/616 |
| 2002/0169209 A1 | 11/2002 | Horrobin ...................... 514/560 |
| 2003/0082275 A1 | 5/2003 | Myhre ............................ 426/72 |
| 2004/0071744 A1 | 4/2004 | Breton et al. ................. 424/401 |
| 2004/0082523 A1 | 4/2004 | Krammer et al. ............... 514/27 |
| 2004/0146539 A1* | 7/2004 | Gupta ........................... 424/401 |
| 2004/0258645 A1 | 12/2004 | Trejo et al. ................. 424/70.13 |
| 2005/0249826 A1 | 11/2005 | Smola |
| 2007/0231371 A1 | 10/2007 | Pan |
| 2008/0057116 A1* | 3/2008 | Pleva ............................ 424/456 |

FOREIGN PATENT DOCUMENTS

| EP | 1 340 427 | 9/2003 |
| FR | 2 815 864 | 5/2002 |
| FR | 2815864 | 5/2002 |
| FR | 2815864 A | 5/2002 |
| FR | 2 821 549 | 9/2002 |
| FR | 2821549 | 9/2002 |
| JP | 04346936 | 12/1992 |
| JP | 2000095683 | 4/2000 |
| JP | 2005015387 | 1/2005 |
| WO | WO0178674 A1 | 10/2001 |
| WO | 01/80870 | 11/2001 |
| WO | 02/11564 | 2/2002 |
| WO | WO0211564 | 2/2002 |
| WO | WO0234210 A | 5/2002 |
| WO | WO0234232 | 5/2002 |
| WO | 02/074308 | 9/2002 |
| WO | 2004/105517 | 12/2004 |
| WO | 2006/056293 | 6/2006 |
| WO | WO2006056293 | 6/2006 |

OTHER PUBLICATIONS

Shahidi, "Soybean Oil", Bailey's Industrial Oil and Fat Products, 2005, vol. 2, 6th Edition, Chapter 13, pp. 578-580.
Higgs et al., "Pharmacokinetics of aspirin and salicylate in relation to inhibition of arachidonate cyclooxygenase and antiinflammatory activity", Proceedings of the National Academy of Science, Mar. 1987, vol. 84, pp. 1417-1420.
Kim et al., "Eicosapentaenoic acid inhibits UV-induced MMP-1 expression in human dermal fibroblasts", Journal of Lipid Research, Aug. 2005, vol. 46, No. 8, pp. 1712-1720.
Kim et al., "Photoprotective and anti-skin-aging effects of eicosapentaenoic acid in human skin in vivo", Journal of Lipid Research, 2006, vol. 47, pp. 921-930.
Levene et al., "Scurvy; a Comparison between Ultrastructural and Biochemical Changes Observed in Cultured Fibroblasts and the Collagen They Synthesise", Virchows Arch B Cell Path, 1977, vol. 23, pp. 325-338.
Murad et al., "Regulation of collagen synthesis by ascorbic acid", Proc. National Academy Science, May 1981, vol. 78, No. 5, pp. 2879-2882.

(Continued)

*Primary Examiner* — Layla Soroush
(74) *Attorney, Agent, or Firm* — Michael P. Aronson

(57) ABSTRACT

A composition which is adapted for oral consumption and which is in the form of a substantially homogeneous aqueous emulsion, suspension or dispersion comprising salicylic acid, or a C1 to C6 alkyl ester thereof, and docosahexaenoic acid (DHA) can exhibit an anti-inflammatory effect in skin.

19 Claims, 1 Drawing Sheet

(56) References Cited

OTHER PUBLICATIONS

Co-pending Application: Casey et al., U.S. Appl. No. 12/752,468, filed Apr. 1, 2010.
European Search Report in EP application EP 10 15 6458 dated Apr. 13, 2010.
PCT International Search Report in PCT application PCT/EP2007/053452 dated Nov. 2, 2007 with Written Opinion.
PCT International Search Report in PCT application PCT/EP2007/052918 dated Mar. 13, 2007 with Written Opinion.
Alestas, Dec. 31, 2005, Enzymes involved in the biosynthesis of leukotriene B4 and prostaglandin E2 are active in sebaceious glands, Journal of Molecular Medicine, 84, 75-87.
Amann, 2002, Anti-inflammatory effects of aspirin and sodium, European Journal of Pharmacology, 447, 1-9, Elsevier.
Baumann, Aug 1055, A dermatologist's opinion on hormone therapy and skin aging, Fertility and Sterility, 84 No. 2, 289-290.
Hankenson, Aug. 10, 1999, Omega-3 fatty acids enhance ligament fibroblast collagen formation in association with changes in Interleukin-6 production, Society for Experimental Biology and Medicine, 223, 88-95.
Jin Young Seo, Jun. 5, 2003, Enhanced expression of cylooxygenase-2 by UV in aged human skin in vivo, Mechanisms of Ageing and Development, 124, 903-910.
Kim et al., Feb. 7, 2006, Photoprotective and anti-skin-aging effects of eicosapentaenoic acid in human skin in vivo, Journal of Lipid Research, 47, 921-930.
Levene, 1977, Scurvy; a Comparison between Ultrastructrual and Biochemical Changes, Virchows Arch. B Cell Path, 23, 325-338.
Maki, 2003, Bioavailability of Eicosapentaenoic and Docosahexaenoic n-3, Journal of Food Science, vol. 68 No. 3, 761-764.
Meydani, Jul. 1993, Immunologic Effects of National Cholesterol Education Panel Step-2 Diets with and without Fish-derived, Journal of Clinical Investigation, 92, 105-113.
Mueller, 2003, Activation of estrogen receptor (alpha) and ER(beta) by 4-methylbenzylidene-camphor in human and rat cells, Toxicology Letters, 142, 89-101.
Murad, May 1981, Regulation of collagen synthesis by ascorbic acid, Proc. National Academy Science, vol. 78 No. 5, 2879-2882.
Reilly, 2000, Inflammatory Mediators in Normal Sensitive and Diseased Skin Types, Acta Derm Venereol, 80, 171-174, Taylor & Francis.
Serhan, Oct. 21, 2002, Resolvins A Family of Bioactive Products of Omega-3 Fatty Acid, Journal of Exp. Medicine, vol. 196 No. 8, 1025-1037, The Rockefeller Press.
Surazynski, 2003, Differential effects of estradiol and raloxifene on collagen biosynthesis in cultured human skin fibroblasts, International Journal of Molecular Medicine, 12, 803-809.
Vahlquist, 2000, Markers of Skin Inflammation and Wound healing, Acta Derm Venereol, 80, 161, Taylor & Francis.
Wei, 2003, Isoflavone Genistein Phtoprotection and Clinical Implications in Dermatology, Journal of Nutrition, vol. 133 No. 11S-1, 3811S-3819S.
Calder, n-3 Polyunsaturated fatty acids, inflammation, and infl, American Journal Clinical Nutrition, 2006, 1505S-1519S, 83, US.
Drenu Chu, Nouvelles Dermatology, Nouvelles Dermatology Translation, 2003, 1-5, ., FR.
Feliciani, Keratinocytes and Cytokine/Growth Factors, Critical Reviews in Oral Biology and Medicine, 1996, 300-318, vol. 7 No. 4, US.
PCT International Search Report in a PCT application PCT/EP2007/053410.
PCT International Search Report in a PCT application PCT/EP2007/053452.
PCT International Search Report in a PCT application PCT/EP22007/052918.
Abstract of FR2 821 549—published Sep. 6, 2002.
Abstract of FR 2 815 864—published May 3, 2003.
Higgs et al., "*Pharmacokinetics of aspirin and salicylate in relation to inhibition of arachidonate cyclooxygenase and anti-inflammatory activity*", Proceedings of the National Academy of Sciences of the United States of America, vol. 84, No. 5, 1987, pp. 1417-1420.
Osnes, et al., "Acetylsalicylic Acid and Sodium Salicylate Inhibit LPS-Induced NF-κB/c-Rel Nuclear Translocation, and Synthesis of Tissue Factor (TF) and Tumor Necrosis Factor alfa (TNF-α) in Human Monocytes", R&D Group, Department of Clinical Chemistry, Ullevaal University Hospital, Oslo Norway, vol. 76, 1996, pp. 970-976.
Yerram et al., "*Eicosapentaenoic acid metabolism in brain microvessel endothelium: effect on prostaglandin formation*", Journal of Lipid Research, vol. 30, No. 11, 1989, pp. 1747-1758.
Calviello et al., "*n-3 PUFAs reduce VEGF expression in human colon cancer cells modulating the COX-2/PGE2 induced ERK-1 and -2 and HIF-1alpha induction pathway*", Carcinogenesis, IRL Press, London, GB, vol. 25, No. 12, Dec. 2004, pp. 2303-2310.
Bousserouel et al., *Different effects of n-6 and n-3 polyunsaturated fatty acids on the activation of rat smooth muscle cells by interleukin-1β*, Journal of Lipid Research, Bethesda, MD, US, vol. 44, No. 3, Mar. 30, 2003 (pp. 601-611).
Rhodes et al., "*Dietary Fish Oil Reduces Basal and Ultraviolet β-generated PGE-2 levels in Skin and Increases the Threshold to Provocation of Polymorphic Light Eruption*", Journal of Investigative Dermatology, vol. 105, No. 4, 1995, pp. 532-535.
Meydani et al., "*Immunologic Effects of National Chloesterol Education Panel Step-2 Diets With and Without Fish-Derived N-3 Fatty Acid Enrichment*", Journal of Clinical Investigation, New York, NY, vol. 92, No. 1, Jul. 1, 1993 (pp. 105-113).
Japanese Abstract JP 2000-095683—published Apr. 4, 2000.
Rhodes et al. "*Dietary Fish-Oil Supplementation in Humans Reduces UVB-Erythemal Sensitivity but Increases Epideral Lipid Peroxidation*", Journal of Investigative Dermatology, vol. 103, No. 2, 1994, pp. 151-154.
Wei, "*Isoflavone Genistein: Photoprotection and Clinical Implications in Dermatology*", vol. 133, No. 11S-I, Nov. 2003 pp. 3811S-3819S.
Rhodes et al., "*Effect of eicosapentaenoic acid, an omega-3 Polyunsaturated fatty acid, on UVR-related cancer risk in humans. An assessment of early genotoxic markers.*", Carcinogenesis (Oxford), vol. 24, No. 5, May 2003, pp. 919-925.
Rhodes et al., "*Systemic eicosapentaenoic acid reduces UVB-induced erythema and p53 induction in skin, while increasing oxidative strees, in a double-blind randomized study*", British Journal of Dermatology, vol. 142, No. 3, Mar. 2000, pp. 601-602.
Shahbakhti et al., "*Influence of eicosapentaenoic acid an omega-3 fatty acid, on ultraviolet-B generation of prostaglandin-E2 and proinflammatory cytokines interleukin-1beta, tumor necrosis factor-alpha, interleukin-6 and interleukin-8 in human skin* in vivo" Photchemistry and Photobiology, vol. 80, No. 2, Sep. 2004, pp. 231-235.
Dreno, "*New methods of evaluation applied to a patented combination of lacto-Lycopene™, soybean isoflavone and vitamin C in the correction of skin aging*", Nouvelles Dermatologiques 2003 France, vol. 22, No. 8, 2003, pp. 557-561 (English abstract attached).
International research Conference on Food, Nutrition, and Cancer; Washington D.C., USA; Jul. 17-18, 2003, ISSN: 0022-3166, p. 3813S.
Co-pending Application: Applicant: Casey et al., U.S. Appl. No. 12/226,165, filed Oct. 29, 2008.
Co-pending Application: Applicant: Casey et al., U.S. Appl. No. 12/226,158, filed Oct. 29, 2008.

\* cited by examiner

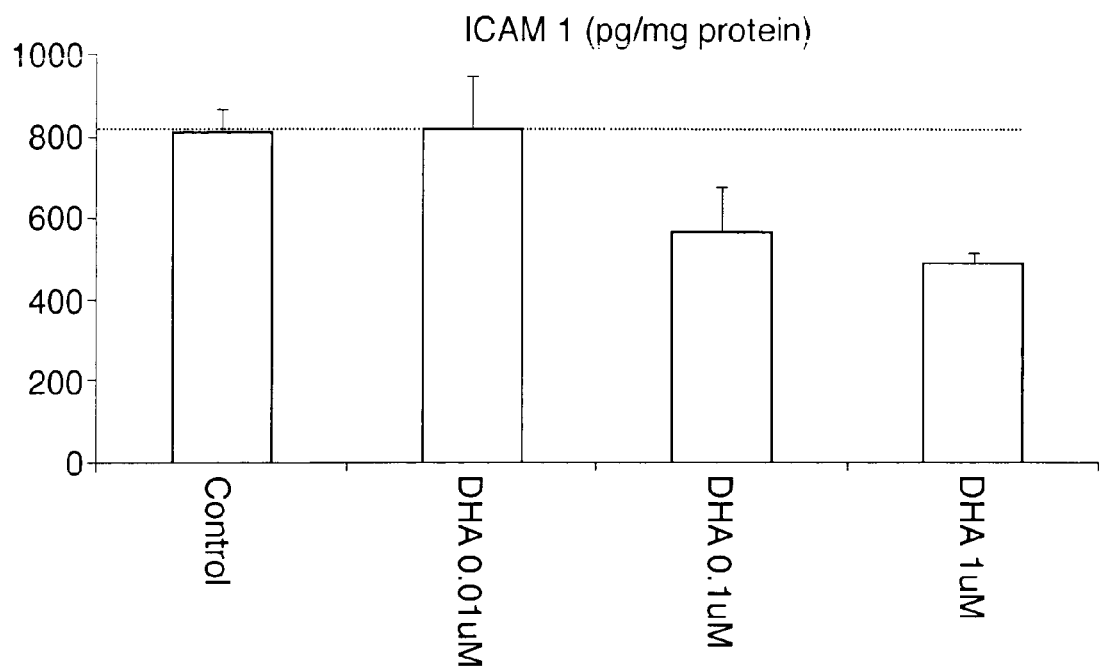
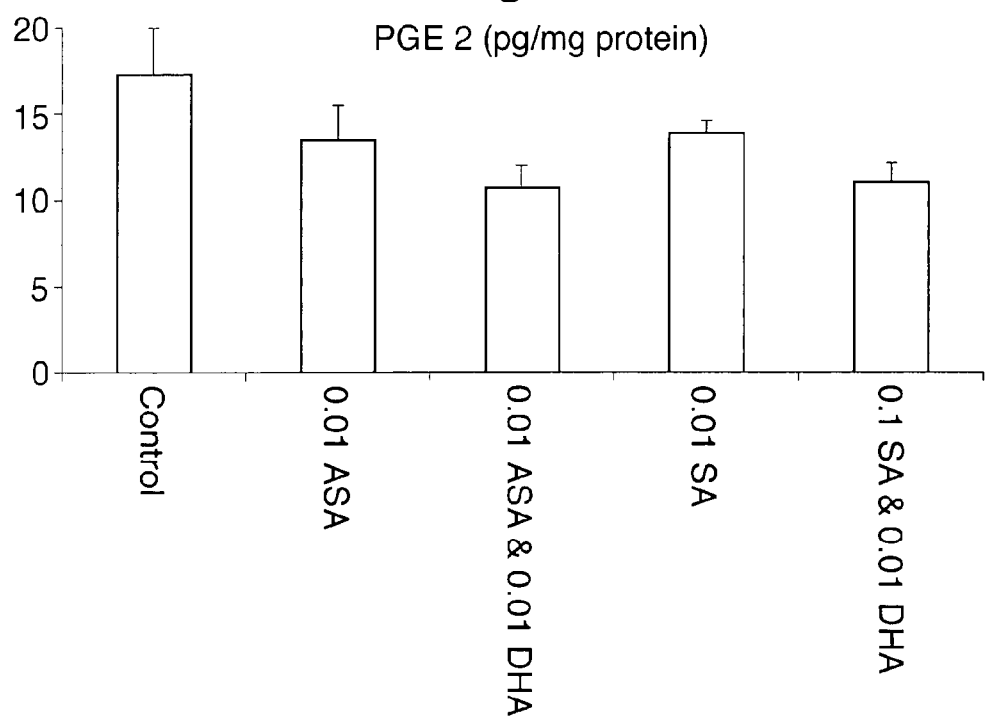

ORAL COMPOSITION COMPRISING A POLYUNSATURATED FATTY ACID AND SALICYLIC ACID FOR OBTAINING AN ANTIINFLAMMATORY EFFECT IN SKIN

The present invention relates to a composition for oral consumption which, when taken orally can have benefits for the skin, and to the use of a combination of active compounds.

Improving the appearance and feel of human skin has received a great deal of research effort. However, the vast majority of commercially available products address this problem by acting on the exterior of the skin, the most common form being a topical skin cream. However, such topical applications have their limitations and deal primarily with the dead surface layers of the skin. It is known that certain ingredients can provide improvements in skin appearance and texture from being ingested. Such ingredients thus act from the interior of the skin and therefore can provide greater opportunities for improving the skin by accessing the living interior. Furthermore such an effect may be perceived by the general public as being more potent or medical in nature than a topical application.

Dietary fish oil is known to convey significant protection against UVR-induced erythema upon ingestion.

Our copending international application no PCT/EP2005/011658 relates to stable consumable emulsions.

Serhan et al, J Exp. Med., 196, no 8, Oct. 21, 2002, 1025-1037 discloses that anti-inflammatory mediators can be formed from docosahexaenoic acid (DHA) in the presence of acetylsalicylic acid (aspirin). The mechanism involved in the production of the anti-inflammatory mediators requires the acetylation of the enzyme cyclooxygenase-2 (COX-2) and the acetyl group in aspirin is therefore essential. Related effects with eicosapentaenoic acid (EPA) are described in Arita et al, JEM, 201, no 5, Mar. 7, 2005, 713-722 and in R&D Systems, Cytokine Bulletin, November 2005 (Abingdon, UK).

US 2002/0054918 discloses topical compositions for treating inflammatory skin conditions. The compositions may be used together with orally administered compositions containing fish oils or aspirin.

US 2004/0258645 describes a personal care kit which has separate containers comprising a topical composition and a product suitable for oral consumption.

WO 02/11564 discloses a nutritional supplement for Type 2 diabetes. The supplements may contain fish oil or aspirin as optional active components. Compositions according to this document are said to include salicylic acid, but it is clear that the document only contemplates or intends the inclusion as an active compound of acetyl salicylic acid, i.e. aspirin, in its compositions.

WO 01/80870 relates to therapeutically useful compositions derived from grapefruit or cranberry. The compositions are said to be useful in the treatment of cancer and hypercholesterolemia. The cranberry extracts contain phenolic compounds and flavonoids and there is no mention of salicylic acid or its derivatives.

There remains a need for orally administered compositions that have improved properties for imparting benefits to the skin of the consumer.

US 2002/0169209 describes pharmaceutical formulations comprising at least 70% eicosapentaenoic acid or acid derivative, less than 10% docosahexaenoic acid or acid derivative and less than 10% linoleic acid or acid derivative, combined in the same dosage form or same pack with an enzyme inhibitor of COX-1 and/or COX-2, LOX or one or more of the FACL enzymes.

According to the invention in a first aspect, there is provided a composition which is adapted for oral consumption comprising salicylic acid, a C1 to C6 alkyl ester thereof or a salt thereof, and a polyunsaturated fatty acid, in an amount sufficient to exhibit an anti-inflammatory effect in skin.

In another aspect, the invention provides the use of salicylic acid, a C1 to C6 alkyl ester thereof or a salt thereof and a polyunsaturated fatty acid in the manufacture of a composition, which is adapted for oral consumption, for obtaining an anti-inflammatory effect in skin.

A further aspect of the invention is a method of reducing inflammation in skin which comprises providing a subject in need thereof with an effective amount of a composition for oral consumption comprising salicylic acid, a C1 to C6 alkyl ester thereof or a salt thereof and a polyunsaturated fatty acid. The subject is preferably a human.

The invention is based on the surprising finding of a synergistic effect between salicyclic acid and a polyunsaturated fatty acid. This effect is particularly surprising because the disclosure in the art indicated that the acetyl group in aspirin was essential for anti-inflammatory activity. It has now been found that salicylic acid can exhibit an anti-inflammatory effect with a polyunsaturated fatty acid when not acetylated.

The composition of the invention thus comprises salicylic acid or a C1 to C6 ester thereof (i.e., without an acetylated phenolic hydroxyl group) or a salt thereof and a polyunsaturated fatty acid. It is preferred that the salicylic acid, or a C1 to C6 alkyl ester or salt thereof, and the polyunsaturated fatty acid are present in an amount sufficient to exhibit an anti-inflammatory effect on the skin.

Compositions of the invention are oral compositions i.e., they are adapted for oral consumption. As such, the compositions are edible and non-toxic.

The composition preferably comprises one or more further components selected from antioxidants, flavouring agents, preservatives and stabilisers.

The composition of the invention may take any suitable form, including, for example, food products and nutritional supplements. Compositions for oral consumption include beverages, bars and other liquid and solid forms such as tablets, pills, capsules and powders (which may contain crystalline material), as well as spreads, margarines, creams, sauces, dressings, mayonnaises, ice creams, fillings, confectioneries and cereals.

Preferably, the compositions of the invention are in the form of a substantially homogeneous aqueous emulsion, suspension or dispersion.

In one embodiment of the invention, the composition of the invention is edible and is preferably water based, i.e. comprises at least 50 wt % water, preferably at least 60 wt % or even at least 70 wt % water. The water may be added or may be derived from a natural product that contains the salicylic acid or ester thereof and/or DHA. It may be either liquid or frozen. The product thus has the sensation of being a regular water-based product and can be consumed on a regular basis as part of a consumer's normal diet. For example, it could replace a fruit juice normally consumed at breakfast time. The composition of the invention is preferably packaged as a beverage, for example in a container such as a carton or a bottle of coated paper or cardboard, glass or plastic. The container preferably has a volume of from 10 to 500 ml, such as from 20 to 100 ml.

In an alternative embodiment, the composition of the invention is contained in a capsule. Typically, the salicylic acid or ester thereof will then be in a more concentrated form. The capsule may be made of any suitable material well known in the art such as gelatin. The capsule is adapted to be swallowed by the consumer and typically one or two capsules will be taken from one to four times per day. Each capsule preferably comprises from 10 to 4000 mg of polyunsaturated fatty acid (more preferably from 10 to 3000 mg or 20 to 2000 mg or 20 to 1000 mg, even more preferably from 50 mg to 500 mg) and from 1 to 100 mg of salicylic acid or a salicylate ester, or a mixture thereof (preferably from 2 mg to 50 mg, such as from 3 mg to 30 mg or from 4 mg to 20 mg).

In a further contemplated embodiment, when the composition of the invention is provided as a tablet, liquid, capsule or powder, the active ingredients in the invention may be distributed across different capsules, tablets, pills or powders, so that for instance the user may be provided with one tablet, capsule, pill or powder containing the salicylic acid or salicylic acid ester/salt, and another tablet, capsule, pill or powder containing the polyunsaturated fatty acid. In such an instance, the user is also ideally provided with instructions to take the liquids, capsules, pills or powders according to a dosage regime, which may entail taking them in the same dose, i.e. at the same time or in quick succession.

In yet a further embodiment, the composition of the invention may be included as one component of a complex food product. For instance, the composition may be present in a solid or gelatinous form as a filling or layer within a bar, or a similar product. The composition of the invention may therefore be included in a wide range of everyday foodstuffs, for instance in "health food" bars which could be eaten as an alternative to other food snacks.

Compositions of the invention comprise salicylic acid, or a C1 to C6 alkyl ester thereof. The term "alkyl" includes saturated, branched or unbranched groups. Typical alkyl groups are methyl and ethyl.

The salicylic acid, esters or salts thereof that are present in the compositions of the invention may and preferably do have a free (e.g. unsubstituted) phenolic hydroxyl group and do not include acetylated derivatives of salicylic acid or its esters such as aspirin. The salicylic acid, ester or salts thereof element in the claims specifically excludes aspirin. The salicylate salt may typically be sodium or potassium salicylate.

Compositions of the invention preferably comprise salicylic acid, a C1 to C6 ester or salt thereof, or a mixture of the acid, one or more esters and/or one or more salts, in an amount of from 0.00002% to 1% by weight, more preferably from 0.00004% to 0.05%, such as from 0.0002% to 0.001% by weight.

Preferably, compositions of the invention comprise from 0.1 to 100 mg of salicylic acid, a salicylate ester or a salicylate salt, or a mixture thereof (preferably from 1 mg to 50 mg, such as from 3 mg to 30 mg or from 4 mg to 20 mg).

Preferably, the salicylic acid, ester or salt thereof is present as a component of a natural product or an extract or concentrate thereof.

The natural product is preferably plant material, for example fruits, more preferably berries, and spices such as cumin. An example of a suitable natural product is cranberry juice; cranberry powder may also be used. Other natural sources of salicylic acid, its esters and salicylate salts are liquorice and herbs, including oregano, rosemary and thyme.

The compositions of the invention comprise a polyunsaturated fatty acid. The fatty acid may be present as a free acid, a C1 to C6 alkyl ester, a glyceride (including mono-, di- and tri-glycerides), or a mixture thereof. Reference herein to polyunsaturated fatty acid includes not only the free acid but esters, glycerides and mixtures. Preferred polyunsaturated fatty acids are those having from 2 to 6, more preferably from 3 to 6, such as 6, carbon-carbon double bonds. Preferred polyunsaturated fatty acids are $\omega$-3 fatty acids. The polyunsaturated fatty acids preferably have from 16 to 24, such as 18 to 22 (e.g., 22) carbon atoms. The most preferred polyunsaturated fatty acid is docosahexaenoic acid (DHA). The DHA is preferably present in the form of a fish oil or is from a microbial source.

DHA is an $\omega$-3, polyunsaturated, 22-carbon fatty acid. It is also present in abundance in certain fish (such as tuna and bluefish) and marine animal oils.

Typically, the amount of polyunsaturated fatty acids (such as DHA) in the compositions of the invention ranges from 0.001% to 4% by weight of the composition. More preferred amounts are from 0.01% to 5% by weight, such as from 0.1% to 1% by weight.

When the DHA is provided by fish oil, the composition of the present invention preferably comprises from 0.2 to 10 wt % of fish oil, more preferably from 0.4 to 4 wt % fish oil. The oil typically comprises DRA and EPA. Preferably, it is made up of at least 12 wt % (such as at least 20 wt %) EPA and DHA, more preferably at least 30 wt % EPA and DHA.

Eicosapentaenoic acid (EPA) is one of several $\omega$-3 fatty acids used by the body. Increased intake of EPA has been shown to be beneficial in coronary heart disease, high blood pressure, and inflammatory disorders such as rheumatoid arthritis.

Eicosapentaenoic acid (EPA) and docosahexaenoic acid (DHA), come from cold water fish such as wild salmon (not farm raised), mackerel, sardines, herring and other northern marine animals. Fish can make EPA and DHA from the $\omega$3 essential fatty acid, alpha-linolenic acid (LNA), but get much of their EPA and DRA from brown and red algae which manufacture EPA and DHA from carbohydrates—sugar, starch, cellulose, etc.

More recently, brown and red algae have begun to be grown commercially for EPA and DHA. These make 10 to 14% of long-chain $\omega$3s (on dry weight basis) and can be used as food sources of EPA and DHA-containing triglycerides.

One or more antioxidants are preferably present in the compositions of the invention in order to prevent or slow down the natural oxidative degradation of the polyunsaturated fatty acid. Rancid fatty acids not only have an unpleasant taste but may even have negative health effects (Kubow S., "Toxicity of dietary lipid peroxidation products", Trends in Food Sciences & Technology, September, 67-71 (1990)).

Suitable antioxidants can be selected, although not exclusively, from the following list, either singularly or in combination: TBHQ, Ascorbyl esters (e.g. ascorbyl palmitate), ascorbic acid, Tocopherols, Rosemary Extract, fruit concentrates or extracts, black or green tea extract, Propyl Gallate, essential oils or oleoresins, butylated hydroxyanisole (BHA), butylated hydroxytoluene (BHT), citric acid or esters, co enzyme Q10, Tocotrienols, Chelators (e.g. EDTA), Carriers, polyphenols, phenolic compounds, flavonoids, oxygen scavengers.

Especially preferred antioxidants are vitamins C and E. Not only are these effective antioxidants but they also have been shown to give skin benefits when consumed.

An amount of antioxidant should be added sufficient to prevent the polyunsaturated fatty acid from going rancid over a typical shelf-life of 6 months. Clearly the amount of antioxidant will depend on the type and activity of the antioxidant used. However, preferably the product has a weight ratio of antioxidant to polyunsaturated fatty acid of from 1:10 to 1:100 based on the antioxidant activity of vitamin C. For example, if an antioxidant with twice the activity of vitamin C was used, the weight ratio would be from 1:20 to 1:200.

For these purposes an antioxidant activity is as measured using an appropriate assay (e.g. Trolox equivalent antioxidant capacity).

The compositions of the invention may comprise a flavouring, although the addition of a flavouring may be unnecessary if the salicylic acid or ester is provided by a flavoured substance such as a fruit juice. Suitable flavouring agents may be natural or synthetic. Flavouring agents may be required to make the product more palatable for consumption.

The compositions preferably comprise an emulsifier, more preferably a food grade phospholipid emulsifier. The emulsifier may be required for stability of a oil-in-water emulsion. It is preferred that the phospholipid emulsifier is lecithin. Phospholipid emulsifiers are oil soluble, but the lecithin can be added to either phase prior to emulsification. Preferably it is added to the aqueous phase.

The emulsifier is preferably present in the composition in an amount of at least 0.01 wt %. Preferably from 0.05 to 3 wt %, more preferably from 0.1 to 1 wt % of the composition.

The composition of the invention may comprise other fatty acids, such as linoleic acid. Linoleic acid may be present as a component of a natural oil, such as a vegetable oil e.g., sunflower oil.

Another optional component of the composition is a detoxifying plant extract, such as rosemary oil.

The composition may also comprise carotenoids, such as in an amount of from 0.0005 to 0.1 wt %, for example from 0.002 to 0.04 wt %. The carotenoids, being oil soluble, would be comprised predominantly within the oil phase. Highly preferred carotenoids are β-carotene, and lycopene. These carotenoids provide moderate protection from UV induced erythema, thought to be due to their antioxidant functionality including scavenging of reactive oxygen species.

The composition may also comprise soy isoflavones (including genistein in glycosylated and/or non-glycosylated form), typically in an amount of from 0.0001% to 0.1% by weight.

The composition of the present invention may be made by preparing an aqueous phase and an oil phase. In general the water-soluble ingredients are put together in the aqueous phase and the oil-soluble ingredients in the oil phase. If an emulsifier is used, it is preferred that it is added to the aqueous phase.

The oil phase and aqueous phase are then blended together to form an emulsion.

In a preferred process the oil is on a powdered carrier material to assist emulsion formation.

The stable emulsion may then be packaged in a sealed container such as a metal, coated cardboard (e.g. tetra Pak) or plastic container. The container is then preferably sealed so as to give no headspace or a gas filled (e.g. nitrogen or carbon dioxide) headspace. This assists still further in preventing oxidation.

Alternatively the emulsion may be frozen and packaged and sold as a frozen consumer product.

The composition of the invention may have an anti-inflammatory effect in skin. Benefits of the anti-inflammatory effects in skin may include one or more of: anti-ageing effects; reduced dryness; increased firmness; increased elasticity; reduced fine lines and wrinkles; fewer spots, pimples and blemishes (including acne); clearer skin; less sensitive skin; and generally healthier skin. The skin may include the skin of the whole body, preferably of the face, neck and/or hands. The skin may also include scalp skin with benefits for hair (including reduced ageing) and scalp itch or irritation. Conveniently, the benefit can be cosmetic.

The composition is preferably used for its anti-ageing and/or anti-wrinkle effects. The skin of the consumer may be described as calm and/or clear and/or blemish-free.

The composition of the invention may be packaged together with a composition for topical application to the skin. As such the composition may be a kit of parts comprising the composition of the invention packaged separately from a composition for topical application to the skin. The kit of parts is adapted to be sold as a single article and to be used by the consumer for consumption of the oral composition and application of the topical composition to the skin. Ideally the kit of parts contains instructions to apply the topical composition and consume the oral as part of a dosage regime, which may require the user to, for example, consume the oral composition and apply the topical composition at set times of the day.

In a further embodiment, the kit of parts may additionally or alternatively comprise a number of separately packaged beverages, wherein the consumer will typically drink one beverage per day. Also within such a kit of parts may be found a composition for topical application to the skin, wherein the quantity of topical composition supplied is intended to provide for use by the consumer for the same number of days as beverages supplied.

The beverage may also be sold in a single package, from which it is intended the consumer drink a measured amount per day.

The topical composition may be provided in amounts which will allow for continued use of the topical composition beyond the time when the beverage has been used, similarly, more beverage may be provided so that this may continue to be consumed beyond the time when the supply of topical composition has run out.

Further, the kit of parts may comprise a packaged product in which different supplements are packaged together, optionally with use instructions, in order to achieve the benefits of the invention. For instance, the kit may comprise capsules, tablets pills and/or powders including separately or in combination salicylic acid, a C1 to C6 alkyl ester thereof and a salt thereof and a polyunsaturated fatty acid. It is possible that this kit would also include a topical composition.

A kit of parts would typically offer a product which could be used for from about 1 week to about 3 months, often about 2 weeks to about 2 months, most preferably for about 1 month.

Where the invention provides a composition for topical application this preferably comprises one or more anti-acne active agents.

Preferably, the anti-acne agent is selected from antibacterials, desquamators, keratolytics and retinoid boosters.

The anti-acne agents are preferably present in the topical compositions in an amount of from about 0.1% to about 20% by weight, more preferably from about 0.1% to about 10%, and most preferably from about 0.1% to about 5% by weight. Anti-acne agents may be single compounds or mixtures of two or more anti-acne agents.

Examples of anti-acne agents include salicylic acid, keratolytics such as sulfur, lactic acid, glycolic, pyruvic acid, urea, resorcinol, alkylresorcinols such as 4-hexylresorcinol, and N-acetylcysteine; retinoids such as retinoic acid and its derivatives (e.g., cis and trans); antimicrobials (including antibiotics and antibacterials), antifungals, antiprotozoals, and antivirals, for example, benzoyl peroxide, octopirox, erythromycin, tetracyclin, triclosan, azelaic acid and its derivatives, phenoxy ethanol and phenoxy proponol, ethylacetate, clindamycin and meclocycline, triclosan, chlorhexidine, tetracycline, neomycin, miconazole hydrochloride, parachlorometaxylenol, nystatin, tolnaftate, clotrimazole, and the like; sebostats such as flavinoids; hydroxy acids; antipruritic drugs including, for example, topically-acceptable salts of methdilizine and trimeprazine; and bile salts such as scymnol sulfate and its derivatives, deoxycholate, and cholate. The compositions may also comprise pantothenic acid or a pantothenic acid derivative, as described in U.S. Pat. No. 5,612,324, the contents of which are incorporated herein by reference.

Preferred components of the topical composition are linoleic acid and/or salicylic acid (or a C1 to C6 ester thereof). Linoleic acid can be included in the composition as part of a natural oil, such as vegetable oil e.g., sunflower oil.

Also useful are non-steroidal anti-inflammatory drugs (NSAIDS). The NSAIDS can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Other examples of compounds that are useful as anti-acne agents, either alone or in combination with the anti-acne agents mentioned above, are retinoid boosters. Retinoid boosters are compounds that mimic the effect of retinoic acid on skin by enhancing the conversion of retinol or retinyl esters to retinoic acid. Retinoid boosters may be used singly or as combinations of two or more compounds. Retinoid boosters are described in WO 02/02074, the contents of which are incorporated herein by reference. Specific retinoid boosters include, for example, ceramides, phosphatidyl choline, linoleic acid, 12-hydroxystearic acid and climbazole.

Optional components of the topical composition include preservatives, antioxidants, fragrances, clays, surfactants, gel-forming materials, silicones, emollients, humectants and pigments. These optional materials may be used singly or two or more of each type of materials may be used (for example, a composition may include two or more different clays). These optional components may be used in admixture e.g., a composition may contain a preservative, a fragrance and a clay.

Specific examples of optional components, some of which are also mentioned hereinafter, are alkyl alcohols containing from 12 to 24 carbon atoms, alkyl carboxylic acids containing from 12 to 24 carbon atoms, polyvinyl pyrrolidone, polyethylene glycol, mineral oil, polysorbates, nonionic surfactants, sorbitol, methyl cellulose, propylene glycol esters, zinc salts, titanium dioxide and mixtures thereof.

The following non-limiting examples illustrate the invention and do not limit its scope in any way. In the examples and throughout this specification, all percentages, parts and ratios are by weight unless indicated otherwise.

EXAMPLES

Example 1

Anti-Inflammatory Synergistic Effect Between Salicylic Acid and DHA in Human Umbilical Vein Endothelial Cells (Huvec's)

Outline of Experimental Approach

An in vitro model has been developed to investigate the impact of cytokine stress on the inflammatory status of endothelial cells.

a. Cells are grown in 6-well (9.5 cm$^2$) plates.
b. The cells are treated with 10 ng/ml Tumour Necrosis Factor alpha (TNF alpha).
c. Tissue culture supernatant and cell pellets were harvested at 24 hours (t24) post-TNF alpha treatment.
d. All tissue culture supernatant was assayed for Lactate Dehydrogenase (LDH), as a measure of cytotoxicity.
e. All cells were counted (Beckman Coulter Counter) and pelleted and cell lysate assayed for Intra Cellular Adhesion Molecule 1 expression (ICAM-1) and Prostaglandin E2 (PGE2).

Materials and Methods

Culture of Endothelial Cells

Huvec cells (Human umbilical vein endothelial cells, TCS Biologicals) were cultured and passaged in EGM-2 (Endothelial growth medium, Biowhittaker) supplemented with heparin, VEGF (vascular endothelial growth factor), gentamicin sulphate, ascorbic acid, HEGF (Human endothelial growth factor), hydrocortisone, HFGF-B (Human fibroblast growth factor B), R3-IGF-1 (long R insulin-like growth factor 1) and FBS (foetal bovine serum).

Cells were routinely plated out in 6-well tissue culture dishes, at a seeding density of about 5000 cells/cm$^2$ in 2 ml complete medium/well, 24 hours before starting the experiment, and incubated at 37° C. in 5% $CO_2$.

Addition of Test Solutions

Test solutions were prepared in EGM-2 containing all supplements except hydrocortisone. Endothelial cells were cells were treated for 24 hours with 10 ng/ml TNF alpha.

Harvesting Samples and Cell Number

Any change in cell morphology was noted before the cells were harvested. Both the tissue culture supernatant and the endothelial cells were harvested after addition of recombinant TNF alpha (t24). All tissue culture supernatants were stored at −20° C.

1 ml of trypsin/EDTA solution (Invitrogen 25300-054) was added to each well, and the plate incubated at 37° C. until the cells detached. 50 µl of this cell suspension was added to 9.95 mls of Isoton II (Beckman Coulter) in an accuvette and 0.5 ml of this suspension was counted twice in a Coulter Particle Counter Z1 with 140 µm aperture.

The remaining 950 µl of original cell suspension was centrifuged at 13000 rpm in a microcentrifuge for 10 minutes. The supernatant was discarded and the cell pellet washed with 500 µl of Dulbecco's PBS and centrifuged as before. The supernatant was discarded as before and cell pellet stored at −20° C. prior to cell lysis. The number of cells per pellet was estimated from the Coulter Counter data.

Cytotoxicity Assay (Promega)

All tissue culture supernatant was examined for cytotoxicity using the Promega CytoTox 96 non-radioactive cytotoxicity assay. This assay quantitatively measures lactate dehydrogenase (LDH) released upon cell lysis and is a good indication of cell viability. 50 µl of tissue culture supernatant or control medium was added to duplicate wells of a 96-well microtitre plate. 50 µl of CytoTox reagent was added and mixed well. The plate was incubated in the dark, at room temperature, for 30 minutes. After this time 50 µl of stop solution was added to each well and the absorbance of the plate was read at 492 nm. Any test samples giving an absorbance value of more than double that of the control medium was considered to be cytotoxic. No results have been included from samples that showed any signs of cytotoxicity.

Preparation of Cell Lysate

All cell pellets were lysed on ice for 30 minutes in 1 ml cell lysis buffer per 2.5×10$^6$ cells. The lysis buffer contained 1% NP-40, 0.1% sodium deoxycholate, 0.1% SDS, 6 mM sodium chloride and 0.05M Tris at pH 7.6. Protease inhibitor cocktail (1000×; Sigma P8340) was added prior to use at a level of 10 µl per ml of lysis buffer. The partially lysed cell pellets were completely homogenised with a pellet pestle and unwanted cell debris removed by centrifugation for 20 minutes at 20,000 g at 4° C. The clarified cell lysate was frozen at −80° C. until needed.

Total Protein Assay (Pierce)

The total protein concentration of each cell lysate was measured using the Pierce BCA protein assay kit. A set of eight standard solutions ranging from 0 to 1200 µg/ml protein was prepared from the supplied 2 mg/ml BSA stock solution. 10 µl of standard or cell lysate was added to duplicate wells of a flat-bottomed, 96-well microtitre plate. The reagent solution was prepared according to the kit instructions from 50 parts reagent A and 1 part reagent B. 200 µl of the final reagent was added to each well of the microtitre plate. The plate was mixed, covered and incubated at 37° C. for 30 minutes and absorbance read at 562 nm. A protein standard curve was constructed and used to determine the protein concentration of each cell lysate.

ICAM-1 ELISA (R&D Systems)

ICAM-1 protein in each cell lysate was estimated using the Human sICAM-1 DuoSet ELISA kit (R&D Systems DY720) according to the manufacturer's instructions.

The capture antibody was diluted to a final concentration of 4 µg/ml in PBS and 100 µl was used to coat each well of a 96-well microtitre plate overnight at room temperature. The plate was then washed three times with wash buffer (0.05% Tween 20 in PBS). Each well received 300 µl of blocking buffer (1% BSA, 5% sucrose and 0.05% sodium azide in PBS), and the plate was incubated at room temperature for 1 hour before being washed as before. Each cell lysate was then diluted 1/200 in reagent diluent (1% BSA in PBS) and 100 µl added to duplicate wells of the antibody coated plate. Eight ICAM-1 standards were prepared in reagent diluent, at concentrations ranging from 0 to 1000 pg/ml, and duplicate 100 µl standards were added to the appropriate wells on the plate. A separate set of standards was routinely used for each plate. The plate was incubated at room temperature for 2 hours before being washed again. 100 µl of detection antibody, diluted to a final concentration of 100 ng/ml, was added to each well and the plate incubated at room temperature for 2 hours. The plate was washed as before. Each well received 100 µl of streptavidin-HRP conjugate diluted 1/200 in reagent diluent and the plate incubated at room temperature, in the dark, for 20 minutes. The plate was washed for the final time and 100 µl of substrate solution (1:1 mixture of colour reagent A and colour reagent B, R&D Systems DY999) was added to each well. After 20 minutes incubation, at room temperature in the dark, the colour development was stopped by the addition of 50 µl of 2N sulphuric acid. The absorbance of the plates was measured at 450 nm with the correction wavelength set at 570 nm.

A standard curve was plotted of mean absorbance versus ICAM-1 concentration and the line of best fit calculated by regression analysis. The unknown concentration of ICAM-1 in the samples was calculated from this, taking the lysate dilution factor into account.

To normalise for differences in cell number and total protein concentration, the final result was expressed as ng ICAM-1 per mg of total protein.

Prostaglandin E2 High Sensitivity ELISA (R&D Systems)

The PGE2 protein concentration of each tissue culture lysate was assayed using the DE2100 Human PGE2 assay (R&D Systems) according to the manufacturer's instructions.

Eight PGE2 standards were prepared in calibrator diluent at concentrations ranging from 0 to 1000 pg/ml. 150 µl of assay diluent and 50 µl of tissue culture lysate or standard was added to duplicate wells. 50 µl of PGE2 HS antibody solution was added to each well and incubated for 18-24 hours at 2-8° C. The plate was then washed four times with wash buffer. 200 µl of pNPP substrate was added to each well and the plate incubated at room temperature for 1 hour at 37° C. 50 ul of stop solution was then added to each well. The optical density of each well was determined using a microplate reader set to 405 nM with wavelength correction set between 570 nM and 590 nM.

A standard curve was plotted of mean RLU versus PGE2 concentration and the line of best fit calculated by regression analysis. The unknown concentration of PGE2 protein in all the samples was estimated from this.

Salicylic acid (SA), acetyl salicylic acid (ASA) and DHA were purchased from Sigma Aldrich.

FIG. 1 shows the dose response inhibition of ICAM-1 with DHA.

FIG. 2 shows the synergy between salicylic acid and a fish oil (DHA) in human umbilical vein endothelial cells in terms of changes in PGE2.

Example 2

Composition of the Invention

The following is an example of a composition of the invention. The composition can be prepared by combining the ingredients and homogenising the mixture.

| Ingredient | Weight % |
| --- | --- |
| DHA | 0.40 |
| Cranberry juice (concentrate) | 50 |
| Vitamin C | 0.17 |
| Vitamin E | 0.25 |
| Lycopene | 0.005 |
| Beta-carotene | 0.002 |
| Soy isoflavones | 0.03 |
| Citric acid | 0.18 |
| Sweetener, thickener, emulsifier | q.v. |
| Water | To 100% |

Example 3

Two Part Composition of the Invention

A composition as described in Example 2 is packaged together with a composition for the topical treatment of skin which can have the following composition.

| Ingredients | Weight % |
| --- | --- |
| Deionized Water | qs 100 |
| Ethanol (SD 40B Alcohol) | 35.0 |
| Salicylic Acid | 2.0 |
| n-Octyl Paraben | 3.0 |
| Glycerol | 2.0 |
| Disodium EDTA | 0.005 |
| Triethanolamine, 99% | 0-1.0 |

Example 4

Packaged Product of the Invention

The following is an alternative example of a composition of the invention. Which may be sold as a packaged product including dosage and use instructions.

The topical treatment of Example 3, intended for application twice daily;

Fish oil capsules each containing 1 gram of fish oil as a source of DHA and EPA at a recommended dosage of 4 capsules per day;

Cranberry powder as a source of salicylic acid at a recommended dosage of 6 grams per day;

Soy isoflavone capsules at a recommended dosage of 100 mg per day.

The invention claimed is:

1. A method of reducing PGE2 induced inflammation in skin which comprises providing a subject in need of a reduction in PGE2 induced inflammation in skin with a composition for oral consumption comprising (a) salicylic acid, a C1 to C6 alkyl ester thereof or a salt thereof and (b) a polyunsaturated fatty acid, wherein the polyunsaturated fatty acid is docosahexaenoic acid (DHA); and wherein the concentrations of component (a) and component (b) present in the oral composition provides a synergistic reduction in prostaglandin E2 (PGE2) when tested in vitro relative to cells treated in oral compositions having like levels of component (a) without component (b) and like levels of component (b) without component (a).

2. A method as claimed in claim 1, wherein the composition is in the form of a substantially homogeneous aqueous emulsion, suspension or dispersion.

3. A method according to claim 1 wherein the salicylic acid salt, ester or salt thereof has a free phenolic hydroxy group.

4. A method as claimed in claim 1 wherein the salicylic acid or ester thereof is present as a component of a natural product or an extract or concentrate thereof.

5. A method as claimed in claim 4, wherein the natural product is plant material.

6. A method as claimed in claim 4, wherein the natural product is selected from fruits, preferably berries, and spices.

7. A method as claimed in claim 6, wherein the natural product is cranberry juice.

8. A method as claimed in claim 1, wherein the DHA is present in the form of a fish oil or is from a microbial source.

9. A method as claimed in claim 1, wherein the composition is in the form of a food product or supplement.

10. A method as claimed in claim 1, wherein the composition is in the form of a tablet, pill, capsule or powder.

11. A method as claimed in claim 1, wherein the composition comprises one or more further components selected from antioxidants, flavouring agents, preservatives and stabilisers.

12. A method as claimed in claim 1, wherein the composition is packaged as a beverage or a bar.

13. A method as described in claim 1 wherein the composition comprises from 0.00002% to 0.05% by weight of salicylic acid, a salicylate ester or a salicylate salt, or a mixture thereof.

14. A method as described in claim 13 wherein the composition comprises from 0.01 to 5% by weight of the polyunsaturated fatty acid.

15. A method as described in claim 1 wherein the composition is in the form of a capsule that comprises from 10 to 4000 mg of polyunsaturated fatty acid and from 1 to 100 mg of salicylic acid or a salicylate ester, or a mixture thereof.

16. A method as described in claim 15 wherein one or two capsules are taken orally by the subject from one to four times per day.

17. A method of providing an anti-inflammatory benefit on the skin which comprises providing a subject in need thereof with a composition for oral consumption comprising (a) salicylic acid, a C1 to C6 alkyl ester thereof or a salt thereof and (b) a polyunsaturated fatty acid, the anti-inflammatory benefit being selected from anti-aging effects; reduced dryness; increased firmness; increased elasticity; reduced fine lines and wrinkles; clearer skin characterised by fewer spots, pimples and blemishes (including acne); less sensitive skin; and generally healthier skin, wherein the polyunsaturated fatty acid is docosahexaenoic acid (DHA), and wherein the anti-inflammatory benefit is associated with a reduction of PGE2-induced inflammation and wherein the concentrations of component (a) and component (b) present in the oral composition provides a synergistic reduction in prostaglandin E2 (PGE2) when tested in vitro relative to cells treated in oral compositions having like levels of component (a) without component (b) and like levels of component (b) without component (a).

18. A method as described in claim 17 wherein the anti-inflammatory benefit is clearer skin characterised by fewer spots, pimples and blemishes (including acne) wherein the clearer skin is associated with a reduction of PGE2-induced inflammation.

19. A method as described in claim 17 wherein the anti-inflammatory benefit is a reduction of fine lines and wrinkles.

* * * * *